US006871087B1

(12) United States Patent
Hughes et al.

(10) Patent No.: US 6,871,087 B1
(45) Date of Patent: Mar. 22, 2005

(54) SUSPENSION DEVICE AND METHOD (75) Inventors: Michael Scott Hughes, Glencoe, MO (US); William Hagen, O'Fallon, MO (US); Mark Boyce, St. Charles, MO (US); Frank M. Fago, Mason, OH (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/513,087

(22) Filed: Feb. 25, 2000

Related U.S. Application Data (63) Continuation-in-part of application No. 09/513,087, filed on Feb. 25, 2000, which is a continuation-in-part of application No. 09/316,315, filed on May 21, 1999, now Pat. No. 6,554,792.

(51) Int. Cl.[7] .............................................. A61B 6/00
(52) U.S. Cl. ......................... 600/431; 604/500; 604/82
(58) Field of Search ............................ 604/500, 82–85, 604/81, 92, 93.01, 13, 140, 150, 181, 183, 187, 218, 523; 600/300, 407, 410, 419–420, 437, 427, 431, 432, 458; 222/145.1, 145.5, 326, 386; 424/95, 952

(56) References Cited

U.S. PATENT DOCUMENTS

| 964,730 A | * | 7/1910 | Ackerman | 604/84 |
|---|---|---|---|---|
| 1,428,043 A | | 9/1922 | Lyons | |
| 3,373,906 A | | 3/1968 | DeHart et al. | 222/235 |
| 3,378,168 A | | 4/1968 | Hildebradt | 222/83 |
| 3,464,412 A | | 9/1969 | Schwartz | 128/218 |
| 3,858,853 A | | 1/1975 | Rausch et al. | 259/40 |
| 4,147,621 A | | 4/1979 | Giddings | 210/22 |
| 4,596,555 A | | 6/1986 | Theeuwes | 604/56 |
| 4,776,704 A | | 10/1988 | Kopunek et al. | 366/184 |
| 4,941,751 A | | 7/1990 | Muhlbauer | 366/176 |
| 5,030,203 A | | 7/1991 | Wolf, Jr. et al. | 604/85 |
| 5,053,019 A | * | 10/1991 | Duffy | 604/232 |
| 5,071,040 A | | 12/1991 | Laptewicz, Jr. | 222/235 |
| 5,246,670 A | | 9/1993 | Haber et al. | 422/102 |
| 5,286,257 A | | 2/1994 | Fischer | 604/82 |
| 5,318,539 A | * | 6/1994 | O'Neil | 604/118 |
| 5,330,426 A | | 7/1994 | Kriesel et al. | 604/89 |
| 5,352,036 A | | 10/1994 | Haber et al. | 366/130 |
| 5,395,323 A | | 3/1995 | Berglund | 604/84 |
| 5,716,339 A | | 2/1998 | Tanaka et al. | 604/82 |
| 5,725,500 A | | 3/1998 | Micheler | 604/82 |
| 5,806,519 A | | 9/1998 | Evans, III et al. | 128/654 |
| 5,891,087 A | | 4/1999 | Ohtani et al. | 604/89 |
| 5,897,530 A | * | 4/1999 | Jackson | 604/132 |
| 6,033,645 A | | 3/2000 | Unger et al. | 424/9.5 |

FOREIGN PATENT DOCUMENTS

| DE | 19625102 | 8/1997 | B01F/5/06 |
|---|---|---|---|
| EP | 0664136 | 7/1995 | A61M/5/28 |
| WO | WO9608227 | 3/1996 | |

* cited by examiner

Primary Examiner—Loan H. Thanh
(74) Attorney, Agent, or Firm—Wood, Herron & Evans, L.L.P.

(57) ABSTRACT

A device and method for providing a suspended agent such as a contrast agent without mechanical resuspension. A volume of agent is divided into sub-volumes in a network of tubes, cells, sponges, grooves, etc. A propellant fluid flows through the network to release the suspended agent. The network may be internal to a container for the propellant fluid. Alternatively, the network may be adjacent an exit port of a container for the propellant fluid, or may be in-line between a propellant fluid container and a patient. The invention reduces sedimentation of agents into one or a few aggregates and eliminates a mechanical mixing step. The invention thus provides a uniformly suspended agent, improving patient health and safety and increasing cost and time savings.

13 Claims, 7 Drawing Sheets

SUSPENSION DEVICE AND METHOD

CROSS-REFERENCES TO RELATED APPLICATIONS

This application is a continuation-in-part of application Ser. No. 09/513,087, filed Feb. 25, 2000, now pending, which is a continuation-in-part of application Ser. No. 09/316,315 filed May 21, 1999, now U.S. Pat. No. 6,554,792.

FIELD OF THE INVENTION

The invention relates to a device and method of using the device for providing a suspended volume of an agent without additional mixing.

BACKGROUND

Agents that do not persist in a suspended state and sediment must be resuspended prior to use. One example of an agent that must be resuspended prior to use is a pharmaceutical colloid, such as a contrast agent that is injected into a patient to enhance an imaging procedure. Contrast agents are used in various types of imaging including x-ray, magnetic resonance imaging (MRI), computed tomography (CT) and ultrasound (US). A contrast agent that comes out of suspension must be resuspended before placing the desired volume to be dosed into a delivery container such as a syringe. If there is a delay before the dose is injected into a patient, for example while preparing the patient or equipment, or if the infusion is extended, the agent must again be suspended before or during administration.

Resuspension of contrast agent requires mechanical manipulations, for example, removing a filled syringe positioned in an injector and remixing its contents. Additional remixing steps may delay a critical infusion time or, if remixing is omitted, the entire imaging procedure may have to be repeated due to suboptimal contrast obtained. Duplicate procedures not only put patients at increased risk and inconvenience, but are also cost- and time-inefficient. Even if the need to resuspend a single bolus injection is not prohibitive for a given procedure, repeated bolus injections or long term continuous infusions can become problematic due to the agent coming out of suspension during administration.

The loss of suspension for a contrast agent at any point in a delivery system to a patient, such as in a syringe and/or in the connecting tubing, severely limits the duration of continuous infusions or the time between intermittent injections. The need to initially resuspend the colloid or other type of agent, and to further suspend if the agent is not used shortly after resuspension, requires either time-consuming effort and vigilance by the user or the use of mechanical mixing devices. In any case, the need to resuspend an agent poses an additional step and a possible source of error in an imaging procedure.

SUMMARY OF THE INVENTION

The invention is directed to a method to control the rate at which a volume of an agent suspended in a fluid is delivered to a patient. The agent, provided in a device having a tubular network and inflow and outflow ports for a fluid to propel the agent, is divided into sub-volumes within the tubular network. By altering the flow to which the agent is exposed, for example, a laminar or non-laminar flow, the rate at which the fluid is delivered is controlled. For example, laminar flow may be altered by changing the density, cross-sectional diameter, length, and/or pitch of the tubular network, and/or by symmetrically or randomly altering the radius of curvature. For example, the radius of curvature and/or density from the inflow port to the center of the device may progressively decrease, and the radius of curvature and/or density from the center of the device to the outflow port may progressively increase. Non-laminar flow may be altered by replacing a circular internal geometry of the tubular network with a non-circular geometry, in a symmetric or random manner and along part of or along the entire network path.

The invention is also directed to a method to control the rate at which a volume of an agent suspended in a fluid is delivered to a patient by providing the agent in a device having a tubular network containing sub-volumes of the agent. The device also contains inflow and outflow ports for fluid to propel agent from the network. The rate is controlled by altering a laminar flow of agent through the network by altering the network density, or by altering a non-laminar flow of agent through the network by replacing a circular internal geometry of a network path with a non-circular geometry.

The invention is also directed to a suspension device that contains a tubular network providing at least one network path and containing sub-volumes of the agent, and has inflow and outflow ports for a fluid to propel agent from the network. The device has a cross-sectional internal geometrical configuration that may be of geometric shape and may be contiguous, non-contiguous, symmetrical or non-symmetrical along the length of the network. The tubular network may have a symmetrically altered radius of curvature, for example, the radius of curvature may increase from an inflow port to the center of the device and may decrease from the center of the device to an outflow port. The tubular network may be a compressible helix, either housed within a container such as a syringe or a network support, or placed in-line. The device may control the rate of agent delivery to a patient, and/or may enhance mixing of the agent.

The invention is also directed to a method and apparatus of decreasing escape of a gaseous agent contained within a suspension device, where the device is a network to contain sub-volumes of the agent and has inflow and outflow ports for a fluid to propel the agent from the network. In the method, one or more devices is provided within a container that is less permeable to the gaseous agent than the network. The apparatus is a container made of a material such as glass or a thick walled plastic such as polyvinyl chloride (PVC) or polypropylene that is less permeable to the gaseous agent than the network.

The invention is also directed to a suspension device for a volume of an agent that is a tubular network arranged in at least two parallel columns, where each column is independently operatively connected and contains sub-volumes of the agent, and inflow and outflow ports for a fluid to propel agent from the network. This embodiment of the device permits the user to adjust the network volume.

The invention is also directed to a method to deliver an agent that contains microbubbles of a pre-determined size. The agent is contained in a suspension device having a tubular network that contains sub-volumes of the agent, and inflow and outflow ports for a fluid to propel agent from the network. In the method, a force exerted on the microbubble-containing agent is altered by exposing the agent to a non-circular internal network geometry.

The invention is also directed to a method to alter a size distribution of microbubbles in a contrast agent injected into a patient by altering a flow rate of the agent between the agent source and an inflow line into the patient.

The invention is also directed to a suspension device for a volume of a contrast imaging agent, such as a microbubble-containing agent. The device is a compressible helical network, for example ½ foot to fifty feet in an uncompressed state, containing sub-volumes of the agent and with inflow and outflow ports for a fluid to propel agent from the network.

The invention is also directed to a method of providing a volume of a suspended agent to a patient by dividing the volume into sub-volumes, storing the sub-volumes in a network, mechanically mixing the agent in the network either before, during or after releasing the agent sub-volumes into a patient through a patient connector by providing a fluid under pressure through the network to propel the suspended agent.

Figure 1:
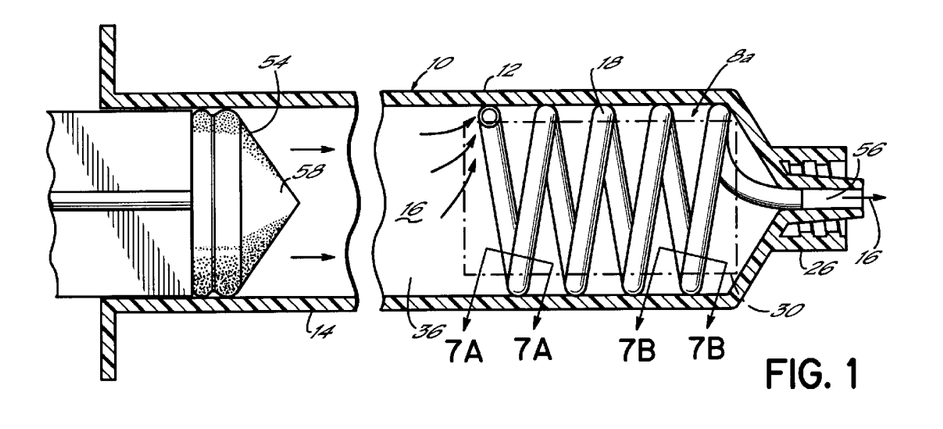
Figure 1A:
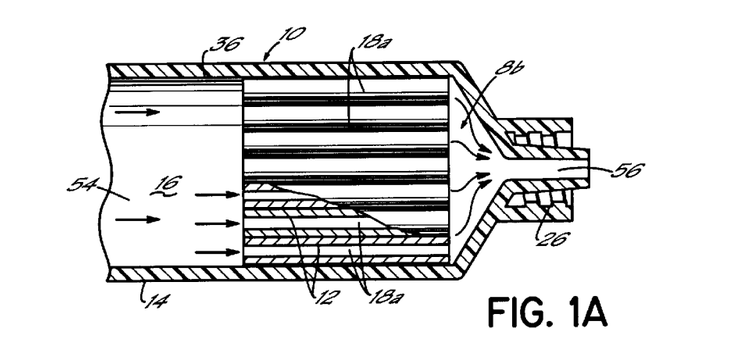

These and other embodiments will become apparent in light of the following figures and detailed description.

helices, an angular or stairstep configuration, and/or even random configurations, or may be arranged in a parallel configuration (FIG. 1A). The geometries and configurations of the network 8 may be combined in either regular or random configurations. While FIGS. 1 and 1A show tubes 18 positioned in a syringe 14 without any accompanying support, other configurations are contemplated. For example, the tubes 18 may be positioned within a network holder 22 (FIGS. 2 and 3), or may be supported or held in a syringe 14 or network holder 22 by a fixture such as 24 (shown in phantom lines in FIG. 1) which may extend for part of or all of the length of the network 8.

Figure 2:
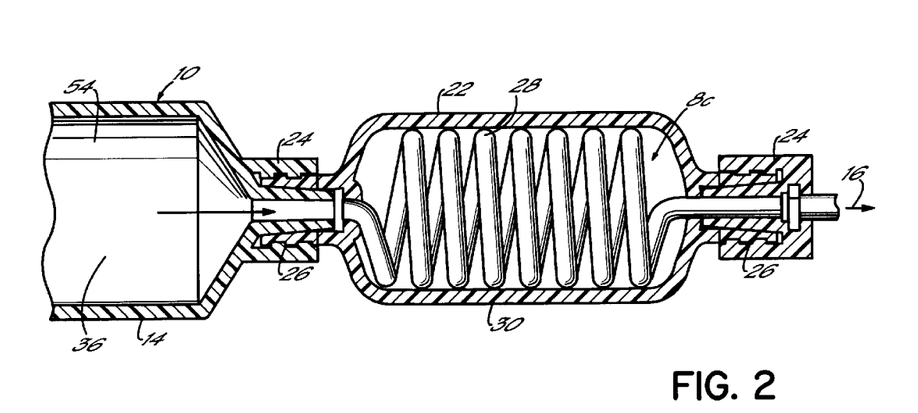

With reference to FIG. 2, a dose delivery container 10 that is a syringe 14 is shown with a network holder 22 containing the network 8 external to the syringe 14. The network 8c is packaged within a network holder 22, which may be any container in which the network is housed or retained and may be made of any biocompatible material. The network holder 22 containing the network 8c may be separable from the syringe 14 or other container 10 and attached to an exit port 24 of the syringe 14 or container 10. The network holder 22 for the network 8c may also be manufactured as part of the container 10, which may be useful as a pre-packaged embodiment of the invention. In a non-pre-packaged embodiment, the network holder 22 may be attached to an exit port 24 using, for example, connectors 26 such as luer fittings. The exit port 24 of the syringe 14 may be fitted with luer fittings, such as Luer-Lok® caps (Becton-Dickinson), or may have luer fittings such as metal, brass or glass luer tips attached. As previously described, a support or fixture 30 for the tubes 28 may be used, and the support 30 and tubes 28 may be contained in a network holder 22. As one alternative, the support 30 and tubes 28 may be contained directly in the container 10. As another alternative, the tubes 28 in a network holder 22 may be unsupported as shown in FIG. 2.

Figure 3:
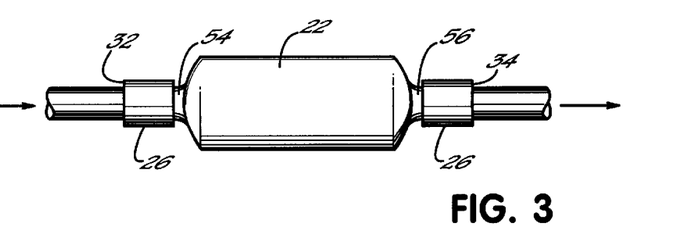
Figure 4A:
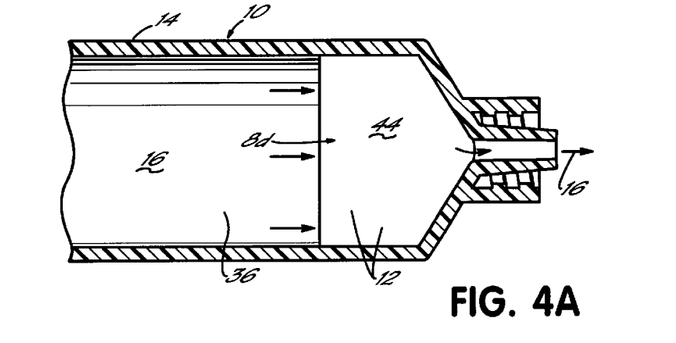
Figure 4B:
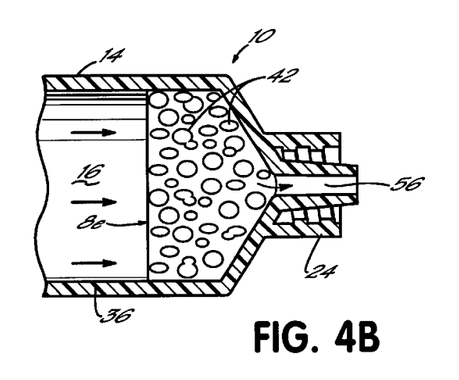
Figure 4C:
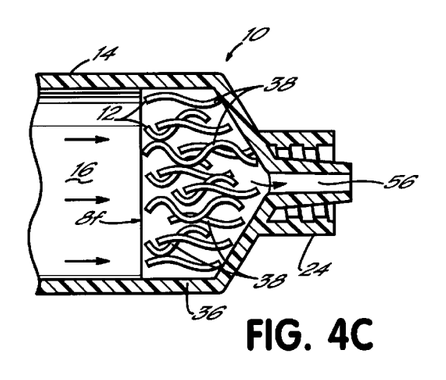

While FIG. 2 illustrates a network holder 22 which is attached to a syringe 14, other embodiments are contemplated. With reference to FIG. 3, the network (not shown) contained in a network holder 22 is shown in an in-line embodiment. The network holder 22 is fashioned with connectors 26 at both an inflow port 32 and an outflow port 34. Tubing is connected to connectors 26 to carry propellant fluid 16 from a syringe to holder 22 and from holder 22 to a patient. The connectors 26 may be the same or different at the inflow 32 and outflow 34 ports and may be any type such as luer fittings, as previously described. Network holder 22 and the network inside may be configured symmetrically, so that the orientation of the network holder 22 in an in-flow embodiment need not be a concern; i.e., there is no back-to-front or front-to-back limitation. Agent 12 can be removed from the network within the network holder 22 upon pressure from a propellant fluid 16.

A network 8 that is internal to a container 10 such as a syringe 14 need not be housed in a network holder 22. As seen in FIGS. 1 and 1A, the network 8a, 8b of tubes 18 or other structures may be positioned directly within the barrel 36 of the syringe 14. In an alternative embodiment, the network 8 that is internal to a syringe 14 or other container 10 may also be housed in a network holder 22. In either embodiment, the barrel 36 of the syringe 14 may contain a propellant fluid 16 that, upon initiation of flow, provides pressure to release or eject the agent 12 from the network 8. The propellant fluid 16 need not be pre-filled in the barrel 36 of the syringe 14, but instead may be added to the barrel 36 of the syringe 14.

The sub-dividing volume structure of tubes 18 in the network 8 may assume a variety of geometries and configurations. As shown in FIGS. 1A, 2, 4A, 4B and 4C, the tubes 18 may be straight, coiled, helical, in random filaments 38, in an angular or stairstep (not shown) configuration, or may have other configurations. All of these alternatives are appropriate for use in any of the illustrated embodiments. The sub-dividing network 8 need not encompass tubes 18 at all; all shown in FIGS. 4A, 4B and 4C, the network 8d, 8e and 8f respectively, may be a series of discrete cells 42 (see FIG. 4B), or may have a sponge 44 type of structure (see FIG. 4A). In a cell 42 structure, the agent 12 is retained in or on discreet cells 42. In a sponge 44 structure, the agent 12 is either absorbed in or adsorbed on the sponge 44, rather than contained within tubes 18 or cells 42. A cell 42 or sponge 44 structure may also be used effectively in a network holder 22 separate from a syringe 14. In any embodiment, the network 8 may be configured so that there is a non-uniform direction for all sub-volumes, that is, there is no single upward, downward or lateral direction for all sub-volumes.

Figure 5:
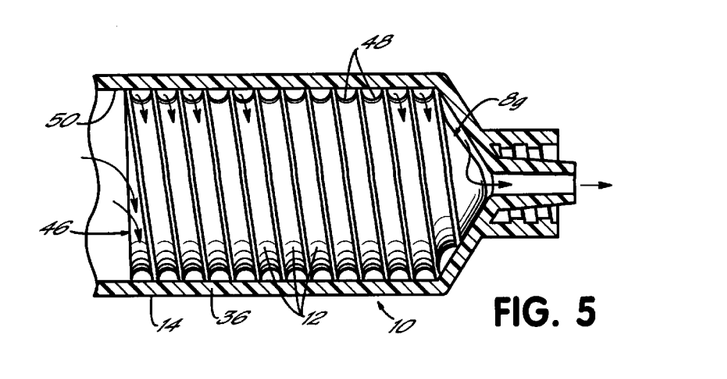
Figure 6:
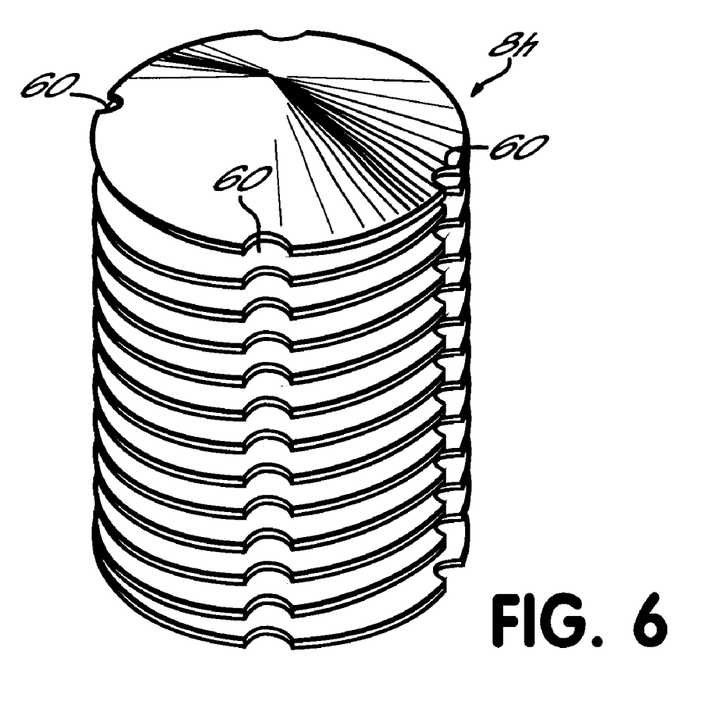

With reference to FIG. 5, a network 8g that is integral with the container 10 is shown. In this embodiment, the network 8g is fabricated as grooves or channels 48 that are etched or otherwise manufactured within the container 10 itself. For example, a syringe 14 may have a cylindrical plug 46 disposed in the barrel 36, where the plug 46 has parallel or spiral grooves 48 in its outer surface. The grooves 48 contain the agent 12 between the syringe 14 inner wall 50 and barrel 36. As shown in FIG. 6, the grooves 48 may contain substantially perpendicular channels 60 at one or more regularly spaced intervals. The channels 60 permit rapid and uniform filling of the network 8 with agent 12 added into one side of a container 10 when the other side of the container 10 is sealed. In another embodiment, the syringe 14 has a cylindrical plug 46 disposed in the barrel 36 as previously described, where the inner wall 50 of the syringe 14 has parallel or spiral grooves in its structure. The grooved structures 48 may also be used in a separate network holder 22. In these embodiments, the grooved structure 48 comprises the network 8 which sub-divides the volume of agent 12. It will thus be appreciated that the network 8 may assume a variety of forms and configurations whereby a volume of agent 12 can be sub-divided into smaller volumes with increased surface area of the agent 12 over which the propellant fluid 16 flows to reduce sedimentation.

The network 8, whether in the form of tubes 18, cells 42 or sponges 44, may be made of any biocompatible material that can withstand sterilization and is inert with respect to the agent 12, the propellant fluid 16, and the container 10. Examples of such materials for a tubular 18 network include biocompatable tubing such as polyethylene, polypropylene, silicon, rubber, etc., for example, Tygon® tubing (halogenated vinyl plastic, Norton Plastics). Tubes 18 used in kidney dialysis devices, such as cellulose tubes 18 having a nominal diameter of 200 μm, may also be used in the invention. In a network 8e having cells or voids, the cells 42 may be produced by incomplete fusion of pieces of fusable material such as thermoplastics or metals. The cells 42 may be made of Delrin™, polycarbonate such as Lexan™, polyethylene, polypropylene, silicon, rubber, etc. In a network 8d having a sponge 44 structure, the sponge 44 may be made of porous Delrin™, porous polycarbonate such as Lexan™, porous polyethylene, porous polypropylene, porous silicon, porous rubber, etc.

The size and volume of the network 8, container 10, and network holder 22 may vary, depending upon a number of factors. These factors include the volume of agent 12, the size of the container 10, the duration of the imaging or other procedure to be performed, etc. There is neither a maximum nor a minimum volume for the network 8, container 10, or network holder 22, and an exponential range of volumes is contemplated by the invention. For embodiments in which the network 8 is internal or integral with the container 10, however, the volume of agent 12 contained within the network 8 is at most one-half the volume of propellant fluid 16 in the container 10. This ensures that substantially all the agent 12 will be released from the network 8 by the flow of propellant fluid 16. For example, volumes of contrast agent 12 injected for enhanced ultrasound imaging may range from 1 ml to about 10 ml. As an example, a 3 ml volume of agent would require using about a 10 ml syringe 14, with the tubular 18 or other structure of the network 8 containing 3 ml agent 12 and the remaining volume of the syringe 14 containing at least 3 ml, and more typically 4–5 ml, of propellant fluid 16. A 3 ml volume of agent 12 may be sub-divided in a syringe 14 having ten threads or grooves 48 per inch, with the threads or grooves 48 one millimeter deep, each thread or groove 48 containing about 0.3 ml agent 12.

The container 10 and/or network holder 22 may be manufactured having the network 8 preloaded with a uniformly mixed suspension of agent 12 such as a pharmaceutical colloid. The container 10 and/or network holder 22 may have both an entry port 54 and an exit port 56 with appropriate fittings 26 such as luer locks for connection to standard tubing or catheters, as is known to one skilled in the art (FIG. 3). To eject the agent 12 in the network 8 from the exit port 56 of the container 10 or network holder 22 and into the patient through a patient connector line, propellant fluid 16 may be injected into the entry port 54 or, alternatively, pressure may be applied to the propellant fluid 16 already in the container 10. The container 10 may also have a single exit port 56 and a plunger 58, with liquid 60 in the opposite end, to permit use as a prefilled syringe (FIG. 1).

The specific location, position and configuration of the network 8 may depend upon an intended use. For example, an agent containing a gas other than air should be housed in a container 10 that has been purged of air. A container 10 made of glass may be rendered air-tight more easily than a plastic syringe, and thus is preferable for this agent. Likewise, a network 8 that is internal rather than external is preferred for use with an agent that contains a gas other than air. This allows the propellant fluid 16 to be purged of air and become saturated with the agent-containing gas, maintaining a substantially anaerobic environment prior to injection.

One advantage of the invention is that it eliminates the need for resuspension of agents 12 that may come out of suspension, either in their original container 10 or in a dose delivery container such as a syringe 14. Conventional containers 10 require mechanical devices or manipulations to maintain colloids such as a contrast agent 12 in suspension. By eliminating the need for prior resuspension of the agent 12 for single-bolus injection, the device and method of the present invention provides a competitive advantage for injectable agents 12. In accordance with the principles of the present invention, a syringe 14 having a network 8 containing agent 12 can remain resuspendable for more than five months.

Maintaining the agent 12 in a substantially fully resuspendable state assures consistent quality and reduced sensitivity to user technique. The agent 12 may be shipped already prepackaged in the network 8. This arrangement has the potential to reduce susceptibility of agents, such as microbubble preparations, to mechanical vibration and shock which may decrease the integrity of the agent 12. Dividing the volume of agent 12 into sub-volumes also allows it to be more quickly preheated to a desired temperature, facilitating the efficiency of the entire imaging procedure.

Another advantage of the invention is that the colloid or other agent 12 may be released, ejected or expelled from the exit port 56 of the container 10 by injecting a propellant fluid 16. This precludes the need to draw the pharmaceutical or contrast agent 12 into a syringe 14 for injection, and provides similar advantages as enjoyed by pre-filled syringes.

Still another advantage of the invention is that, in those embodiments such as FIGS. 2 and 3 where network 8 is external to the syringe 14, the exit port 56 of the dose delivery container 10 or network holder 22 may be connected to a short angiocatheter (not shown) that is very close to a venous or arterial puncture site in a patient. This arrangement prevents loss of suspension of agent 12 that would occur inside a longer catheter, and permits use of a manual or power syringe located a substantial distance away from the patient, while preventing the need for the agent 12 to maintain resuspendable in the manual or power syringe 14 and connecting tubing. Instead, the manual or power syringe and tubing need only contain a non-colloidal fluid that does not require mixing or resuspending during long injection times.

A further advantage of the invention is realized with an optional built-in plunger 58 in the syringe 14. A built-in plunger 58 permits use of the device as a manual syringe 14 or with a small, battery-operated power injector at the end of a very short angiocatheter. In either case, the filled syringe 14 could be located very close to a venous or arterial puncture site, precluding the need to maintain the agent 12 resuspended in a long catheter for infusion into a patient. This embodiment also precludes the need for a fluid-filled syringe 14 connected to the entry port 54 of the dose delivery container 10 in order to eject the agent 12 from the exit port 56 of the dose delivery container 10.

Mixing of the agent 12 flowing through a network 8 having a tubular structure 18a–b, also called a tubular network 18, may be achieved by varying the intrinsic and/or extrinsic geometries of the tubes 18a–b. The effectiveness of mixing increases or decreases with alterations in the network cross-sectional geometry. Any change which increases flow velocity or turbulence will improve mixing. Since mixing of agent 12 can be accomplished by either turbulent flow (defined as the motion of a fluid having local velocities and pressures that fluctuate randomly) or non-turbulent (also called laminar) flow, providing configurations of tubes 18a–b that enhance either or both types of flow will promote mixing.

Interlaminar mixing may be promoted by altering the gravitational orientation of the agent 12 suspended as sub-volumes in the tubular network 18, or by altering turbulent flow. In an agent containing microbubbles, the agent may be thought of as being divided into sub-volumes which each contain a subset of the total number of microbubbles. Over short time intervals most of the microbubbles in a given sub-volume will tend to remain in the same sub-volume as agent flows through the network. As the various sub-volumes of agent flow through the network, the orientation will continuously vary between up and down as the sub-volume flows through the network. In effect, this results in the sub-volume being turned upside down, then downside up, then back to upside down, and so on. This mechanism promotes mixing of the microbubbles within a given sub-volume.

Figure 7A:
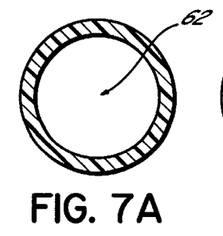
Figure 7B:
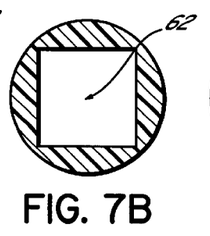
Figure 7C:
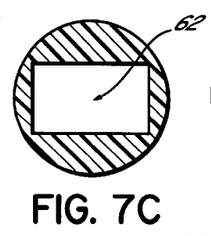
Figure 7D:
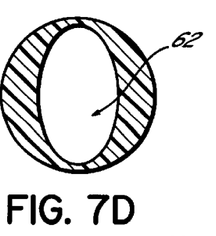
Figure 7E:
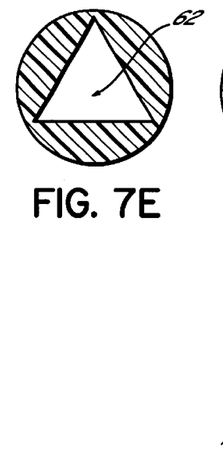
Figure 7F:
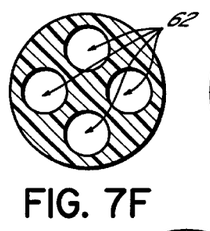
Figure 7G:
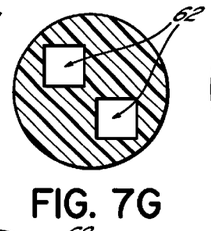
Figure 7H:
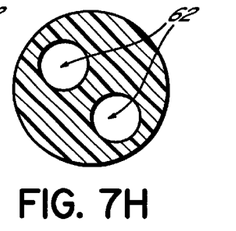
Figure 7I:
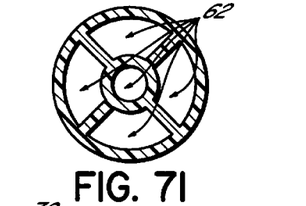
Figure 12A:
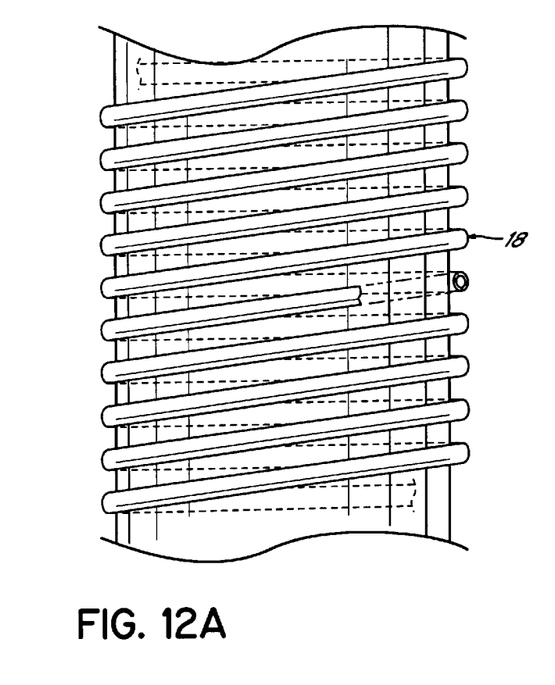
Figure 12B:
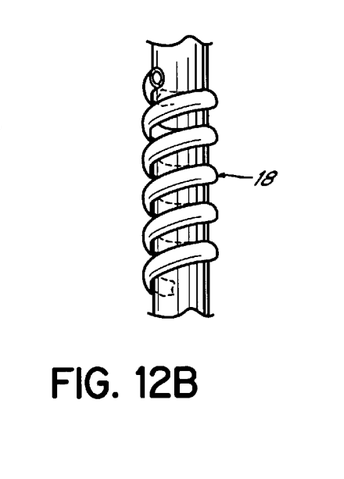

Turbulent flow may occur by exposing the agent 12 to one or a number of intrinsic geometries within the internal surface of the network. For example, and with reference to FIGS. 7A, 7B, 7 network volume of contained agent per defined area, in contrast to a high density network (FIG. 12B), which is one having a relatively greater network volume of contained agent in the same defined area. For example, in a tubular network, tubes that are of identical sizes may be configured to have a smaller radius of curvature (for example, a radius of curvature of ⅛ inch) around a fixture. This would result in greater mixing of a contained agent than tubes 18 configured to have a larger radius of curvature (for example, a radius of curvature of one inch) around a fixture having the same internal channel geometry. This is because the agent flowing through a ⅛ inch tubular network is exposed to a greater centrifugal force in negotiating a greater number of curves than an agent flowing through a one inch tubular network.

Enhanced mixing may also be achieved by other means, for example, by altering the diameter of the channels through which the agent flows in the network, altering the pitch of grooves (that is, the distance between repairing turns on a line drawn parallel to a helical axis) in a symmetrical or partially symmetrical network configuration, and/or altering the length of the tubular network. A longer, thinner tubular network has a higher ambient pressure than a shorter wider network having the same total area. If an agent contains microbubbles suspended in a liquid, this configuration impacts the hydrostatic pressure to which the microbubbles are exposed, which in turn affects the microbubble size distribution infused into a patient. The following example, not shown in the figures, illustrates this concept.

A total volume of 1.5 ml of a microbubble-containing agent is contained in a tube having a cross-section of 0.015 inch, and wound as tightly as possible (that is, at relatively high density) around a ⅛ inch diameter rod-shaped fixture that is two feet long (that is, a total of two feet of wound tubing). If the agent is viscous, the agent will have to be subjected to increased pressure (overpressured) to flow through the tubular network. However, overpressurization collapses microbubbles of all sizes in the agent, and once the smallest sized microbubbles collapse, there is no nucleation site for exchange of the gas contained within the microbubbles. Since these smallest sized microbubbles cannot be regenerated, they are permanently removed from the agent under these conditions.

In comparison, a total volume of 6 ml of a microbubble-containing agent is contained in a tubular network having a cross-section of 0.034 inch, and wound as tightly as possible (that is, at relatively high density) around a 3/16 inch diameter rod-shaped fixture that is two feet long (that is, a total of two feet of wound tubing). Under these conditions, even if the agent is viscous, the agent will not have to be subjected to increased pressure (overpressured) to flow through this network. Thus, no microbubbles will be collapsed and an agent containing microbubbles of all sizes will be delivered and infused into the patient.

There is, however, a trade-off between the length of the network and the cross section of the network that is independent of the volume contained. While one can obtain any volume desired if the cross-section of the network is increased sufficiently, once the cross-section is increased above a certain point, the microbubbles become trapped or hung up in the network and hence do not reach the patient.

Figure 8A:
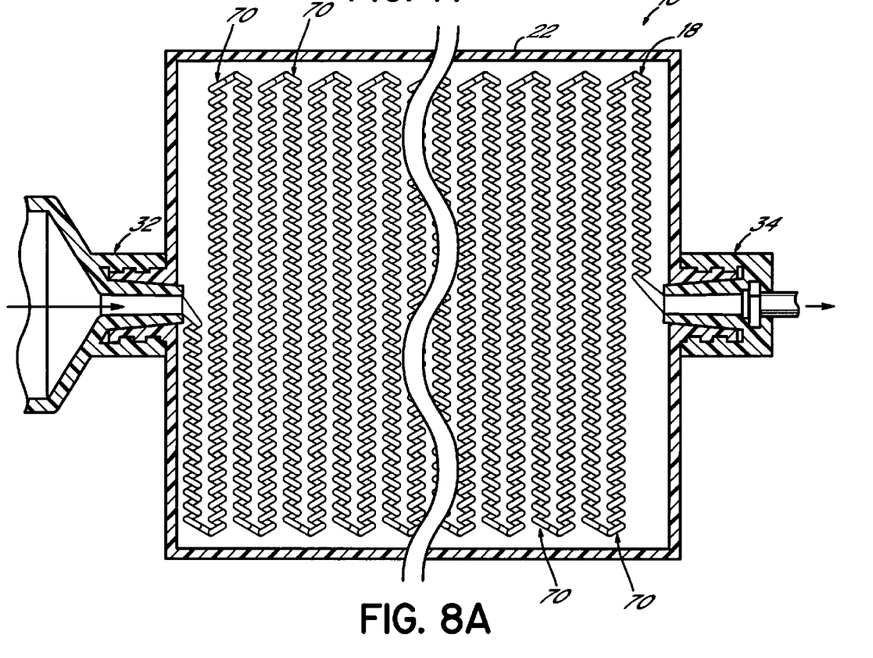
Figure 8B:
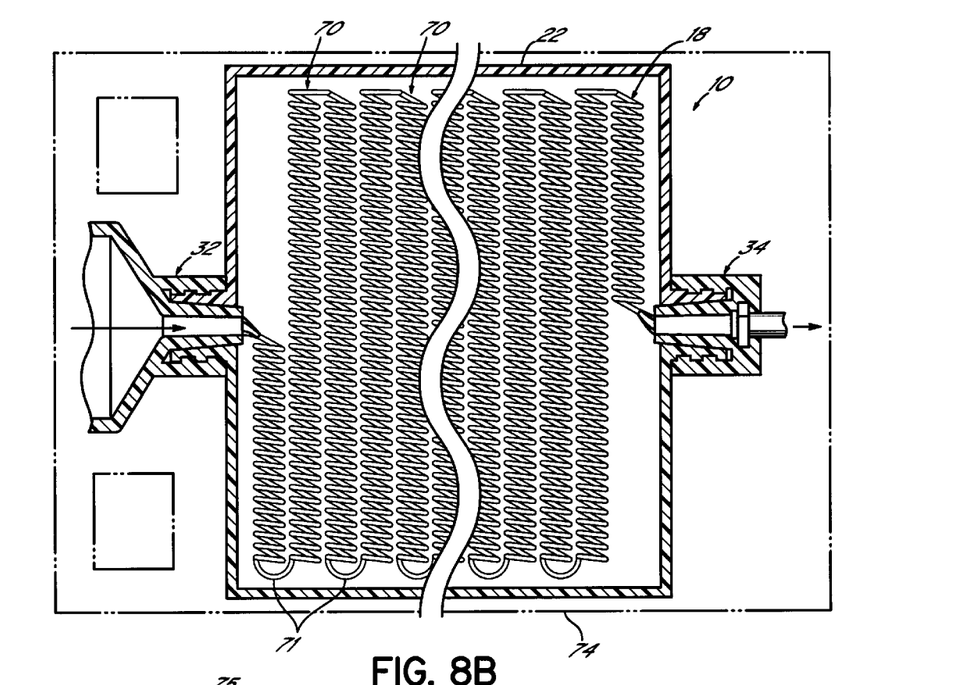
Figures 9, 10:
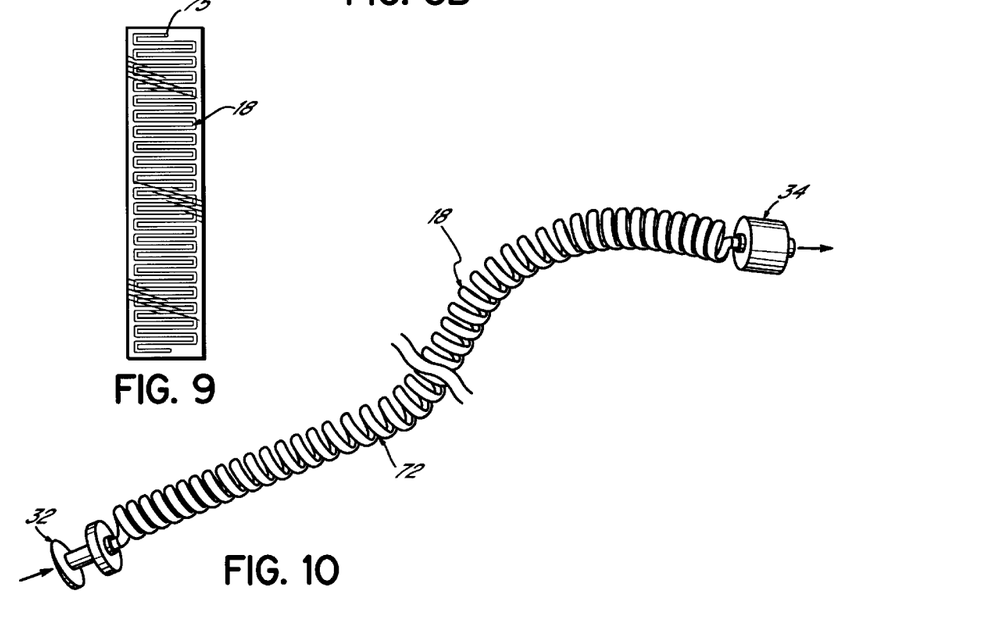
Figure 11:
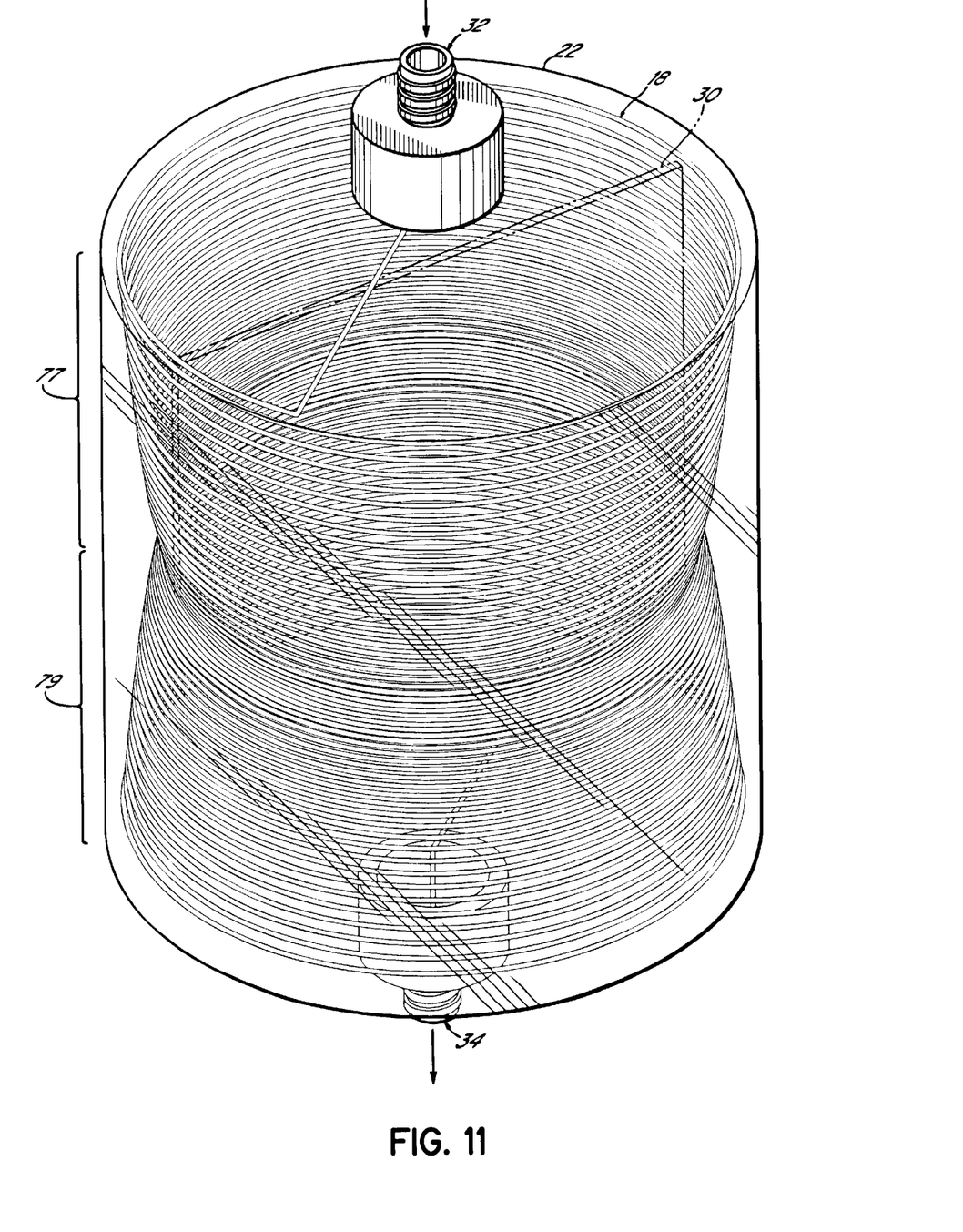

In other embodiments, the composition of the tubular network 18 and/or network holder 22 may be altered to achieve a desired effect. For example, the network 18 and/or network holder 22 may be made of a material that protects a gaseous agent 12 contained in the network 18 from a gaseous exchange, and hence protects the integrity of the agent 12. An example of this would be a network 18 composed of a material that is less permeable or even impermeable to gas, thus decreasing gas exchange. As an alternate example, the network 18, either of a typical material or a material that is less permeable or impermeable to gas exchange, may be packaged in a secondary container 74, as shown in phantom in FIG. 8A, that is less permeable or impermeable to gas exchange, to achieve the same or similar effect. This would increase protection for agents which are sensitive to air. The secondary container 74 may be glass or a thick walled (greater than ¼ inch) plastic such as polyvinyl chloride (PVC), polypropylene, or other material that may be sterilized using gamma irradiation. Alternatively, one secondary container 74 may contain a plurality of less expensive but gas permeable containers (multi-unit packaging). This advantageously provides a secondary container 74 that is less permeable or impermeable to gas exchange, but reduces the expense of providing such a container 74 for each network 18 or network holder 22. In still another embodiment, a secondary container 74 may itself contain a gas that is the same as, or compatible with, the gas contained in the microbubbles to further decrease gas exchange and to maintain integrity of a gaseous agent, such as a microbubble-containing agent 12.

Another embodiment of the invention is the use of an inventive resuspension device in combination with a mechanical resuspension device such as a mixing apparatus (not shown). This may be advantageously used when a tubular network is being filled with an agent, for example, when a non-prefilled network embodiment is used. This embodiment may also be used when filling must occur over a period of time, during which the agent may come out of suspension, and the user desires to maintain the agent in a suspended state throughout the filling process. Additionally, this embodiment may be used when a very large volume of agent is to be delivered to a patient and the volume of agent exceeds the capacity of the network, necessitating a volume greater than the network capacity. In this case, a mechanical suspension device may be used that is small enough to be proximal to an infusion site in a patient, for example, that is taped to a patient's arm or leg, to maintain suspension of agent.

The device may be used to control the rate of delivery of sedimenting agents such as pharmaceutical colloids to a patient. Heretofore, it was not appreciated that altering the flow rate of a microbubble-containing agent would alter the normal size-distribution curve of the microbubbles in the volume of agent, and hence would alter the size distribution of the contained microbubbles that are delivered into a patient. If the agent is comprised of a plurality of microbubbles, such as a contrast agent containing a plurality of microbubbles suspended in a liquid, the rate at which the agent is delivered may be used to control the size of microbubbles that are injected into the patient. This advantageously excludes microbubbles that are above a set threshold size, which may have deleterious effects if they are injected into a patient. Also, depending upon the type of imaging procedure that a patient is to undergo and the particular organ or tissue to be imaged, infusion of microbubbles limited to a certain size range is desirable. As one example, in renal, hepatic and ocular imaging, only relatively small microbubbles in the range of about 2 $\mu$m to 4 $\mu$m should be administered, due to the small microvascular network in the kidney, liver, and eye, respectively. As another example, the clinician or technician is able to alter the microbubble size and distribution to achieve, for example, an altered backscatter or an altered attenuation. This permits the technician or clinician to make fine adjustments to the image in real time, that is, as the imaging is in progress and during infusion of the agent into the patient. As the image is being displayed and evaluated, alteration of the image quality by alteration of the delivery rate will result in images of higher diagnostic significance, and hence the imaging procedure will be of a higher diagnostic value and be more cost- and time-efficient.

This would be applicable for use in a single bolus injection of a microbubble-containing agent, as well as a continuous infusion of agent.

Control of the rate at which the agent is delivered, resulting in control of the particle size of microbubbles in an agent, is accomplished by altering the cross sectional geometry of the tubular network. Using the inventive device, the technician or clinician thus controls the profile of shear forces and mixing turbulence of the agent within the network. This impacts the hydrostatic pressure on the microbubbles, which in turn alters the flow rate of the agent through the network and in turn affects the size distribution of microbubbles reaching the infusion site and being injected into the patient.

The pressure at which the agent containing microbubbles flows through the network may also be controlled to achieve altered size distribution. Since microbubbles flow through the network at a defined hydrostatic pressure, alteration of the ambient hydrostatic pressure, either by constant or variable alteration, exposes the microbubbles to a different hydrostatic pressure at any given time.

It should be understood that the embodiments of the present invention shown and described in the specification are exemplary embodiments contemplated by the inventor and are not limiting in any way. For example, the invention is not limited to use in the clinical area and may be used in research applications, as well as in other industries where uniformly suspended agents are needed, such as the food and beverage industries. In such cases, for example, the propellant fluids 16 may also include oils, epoxy resins, sugars, etc., depending upon the application. Therefore, various changes, modifications or alterations to these embodiments may be made or resorted to without departing from the spirit of the invention and the scope of the following claims.

What is claimed is:

1. An administration method for an injectable suspended agent containing microbubbles, comprising:
   providing the agent in a helical tubular network;
   providing network ports for an inflow and an outflow of a fluid to suspend and propel the agent from the tubular network;
   altering a laminar flow to which the agent is exposed thereby promoting mixing of the microbubbles in the suspendable agent, said laminar flow being altered by altering a property of the tubular network selected from the group consisting of density, cross-sectional diameter, length, pitch, and combinations thereof; and
   administering the mixed suspended agent to a patient.

2. An administration method for an injectable agent comprising:
   providing the agent containing microbubbles in a tubular network and ports for an inflow and an outflow of a fluid to propel the agent from the network; and
   altering a force on the agent by exposing the agent to a non-circular internal geometry along at least a portion of a length of the tubular network to selectively administer the agent and microbubbles of a pre-determined size in the agent to a patient.

3. An administration method for an injectable suspended agent comprising:
   providing the agent containing microbubbles in a container capable of connecting to a patient connector;
   providing pressure to the agent to initiate a flow rate of the agent between the container and the patient connector; and
   altering the flow rate of the agent between the container and the patient connector thereby altering the size of microbubbles administered to a patient.

4. The administration method of claim 3 wherein said flow rate is controlled by altering a laminar flow.

5. The administration method of claim 3 wherein said flow rate is controlled by altering a non-laminar flow.

6. The administration method of claim 3 wherein said flow rate is controlled by altering gravitationally-promoted interlaminar mixing.

7. An administration method for a suspendable agent containing microbubbles, comprising:
   altering a laminar flow of the agent moving through a helical tubular network to promote mixing of the microbubbles in the suspendable agent by varying a radius of curvature of the helical tubular network; and
   administering the mixed agent, after the laminar flow is altered, from the helical tubular network to a patient.

8. An administration method for a suspendable agent containing microbubbles, comprising:
   altering a laminar flow of the agent moving through a helical tubular network to promote mixing of the microbubbles in the suspendable agent by arranging the helical tubular network in a plurality of columns; and
   administering the mixed agent, after the laminar flow is altered, from the helical tubular network to a patient.

9. An administration method for a suspendable agent comprising:
   altering a laminar flow of the agent moving through a helical tubular network to promote mixing of the microbubbles in the suspendable agent by varying a network density of the helical tubular network; and
   administering the mixed agent, after the laminar flow is altered, from the helical tubular network to a patient.

10. An administration method for an injectable suspended agent containing microbubbles, comprising:
    providing the agent in a tubular network;
    providing network ports for an inflow and an outflow of a fluid to suspend and propel the agent from the tubular network;
    altering a non-laminar flow to which the agent is exposed thereby controlling a rate at which the agent is administered, said non-laminar flow being altered by exposing the flowing agent to a first internal geometry along a first length of the tubular network and to a second internal geometry along a second length of the tubular network that differs from the first geometry; and
    administering the mixed agent, after the non-laminar flow is altered, from the tubular network to a patient.

11. The method of claim 10 wherein said first internal geometry is circular and said second internal geometry is selected from the group consisting of circular, square, elliptical, triangular, rectangular, and wedge-shaped.

12. The method of claim 10 wherein at least one of said first and said second internal geometries is characterized by a plurality of lumens.

13. The method of claim 10 wherein said first and said second internal geometries are each selected from the group consisting of circular, square, elliptical, triangular, rectangular, and wedge-shaped.

* * * * *

UNITED STATES PATENT AND TRADEMARK OFFICE
CERTIFICATE OF CORRECTION

PATENT NO. : 6,871,087 B1
DATED : March 22, 2005
INVENTOR(S) : Hughes et al.

It is certified that error appears in the above-identified patent and that said Letters Patent is hereby corrected as shown below:

<u>Column 13,</u>
Lines 59-60, "... to selectively administer the agent and microbubbles..." should be
-- ... to selectively administer the mixed agent with the agent and microbubbles --.

<u>Column 14,</u>
Line 52, "... is altered, from the tubular network to a patient." should be -- ...is altered, from the helical tubular network to a patient. --.

Signed and Sealed this

Twenty-fifth Day of October, 2005

JON W. DUDAS
*Director of the United States Patent and Trademark Office*